United States Patent [19]

Montealegre

[11] 4,280,649

[45] Jul. 28, 1981

[54] AIR FRESHENER CARTON

[75] Inventor: James Montealegre, W. St. Paul, Minn.

[73] Assignee: Champion International Corporation, Stamford, Conn.

[21] Appl. No.: 108,023

[22] Filed: Dec. 28, 1979

[51] Int. Cl.³ .................. B65D 13/04; A61L 9/04
[52] U.S. Cl. .................................... 229/11; 239/57
[58] Field of Search .................. 229/9, 10, 11, 19, 20, 229/23 BT; 239/59, 60

[56] References Cited

U.S. PATENT DOCUMENTS

| 2,929,542 | 3/1960 | O'Gorman | 229/11 |
| 3,302,844 | 2/1967 | Henry | 229/10 |
| 4,220,028 | 9/1980 | Martens et al. | 229/11 X |

FOREIGN PATENT DOCUMENTS

| 732939 | 4/1966 | Canada | 229/11 |
| 467044 | 11/1951 | Italy | 229/11 |

Primary Examiner—Davis T. Moorhead
Attorney, Agent, or Firm—Evelyn M. Sommer

[57] ABSTRACT

A carton for selectively diffusing an air freshener material to the atmosphere includes a first imperforate outer sleeve open at opposite longitudinal ends slidably receiving a second inner sleeve therethrough housing a cake of air freshener. The second sleeve includes a plurality of openings on the lower half of the sleeve which are selectively opened and closed by movement of the first imperforate sleeve relative to the second sleeve. The second, inner sleeve has a sealed closure at opposite ends including a panel extending beyond the side walls thereof for abutment with the upper and lower edges of the first outer sleeve to preclude disassembly of the first and second sleeves.

3 Claims, 9 Drawing Figures

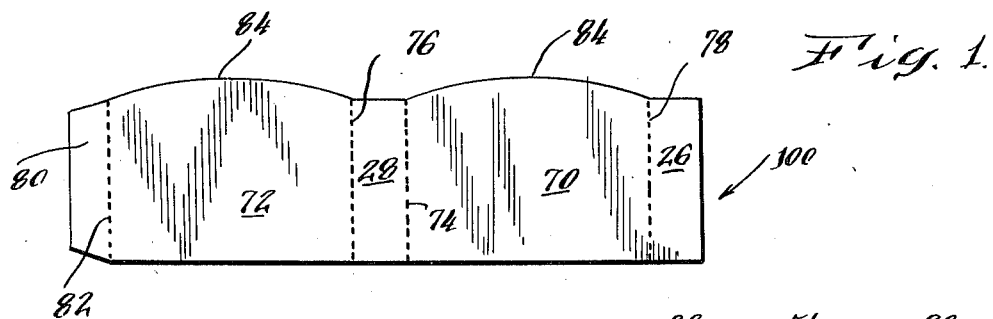
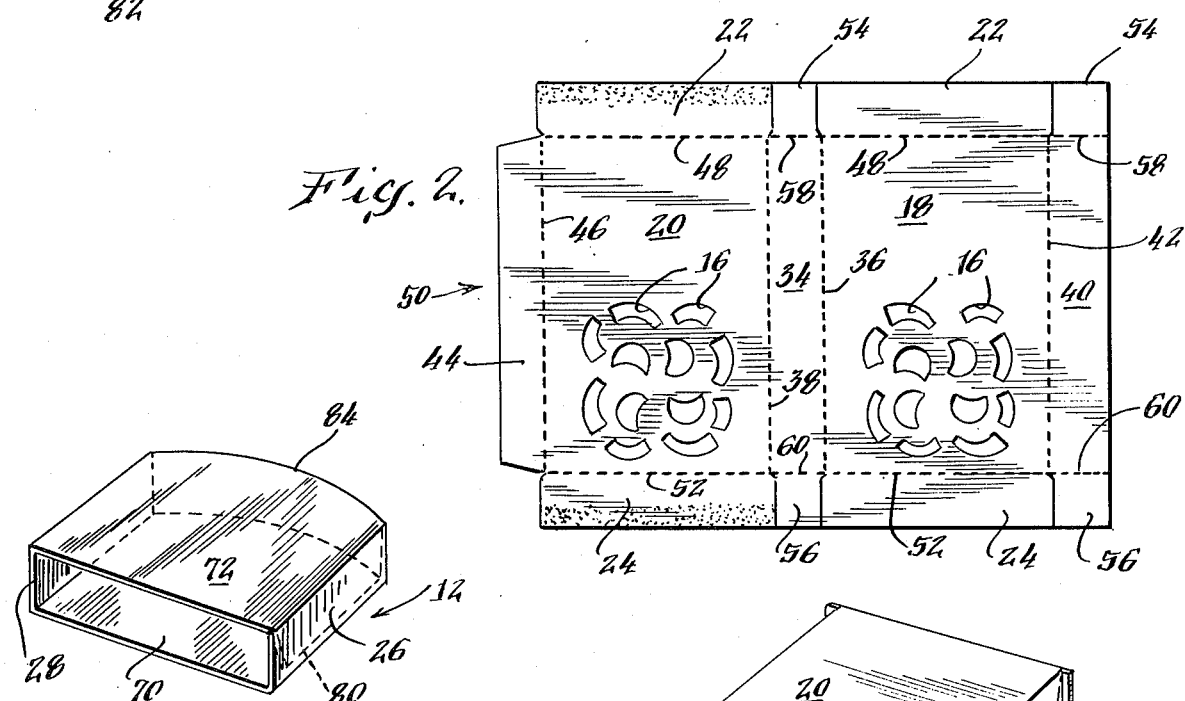
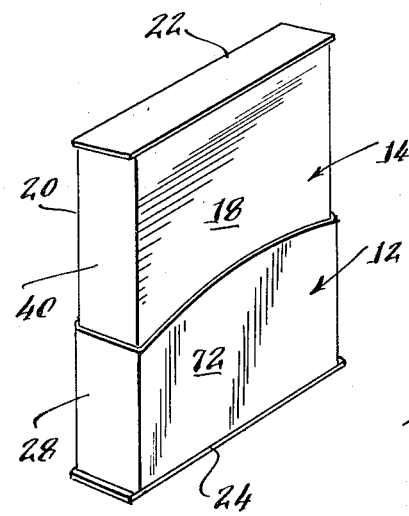
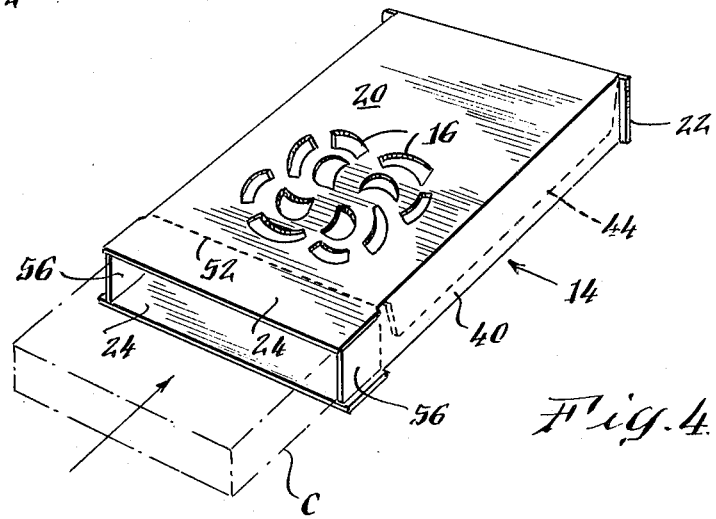

AIR FRESHENER CARTON

BACKGROUND OF THE INVENTION

1. Field of Invention

The present invention relates to cartons, and more particularly to a carton for holding an active material and controllably releasing it to the air.

2. Description of the Prior Art

There are a variety of active materials for use in household and commercial applications which it is desirable to contact with and release into the ambient air. Among these are insecticides and air fresheners which can be packaged in solid form in containers having air passages which permit release. Frequently, products of this type are packaged in containers having a plurality of openings which are closed at the time of purchase but which are opened at the time of use to allow room air to circulate over the surface of the solid active material.

In one type of carton, the openings are covered with a panel of release paper. When the consumer is ready to use the product, such as an air freshener, the release paper is peeled from the face of the container to allow room air to begin circulating through the openings. In another type of carton, the consumer activates the air freshener material by squeezing to release an encapsulated active ingredient. In yet another type of carton, holes in an outer carton wall are opened or closed by a slidable inner sheet which acts as a valve.

Molded plastic containers, usually consisting of a molded shell and a separate molded cover, have been employed to hold air freshener material. However, while molded plastic containers have an aesthetically pleasing appearance, the cost of making them is higher than might be desired. The shell and cover must be molded in separate operations and stored in unassembled form until the air freshener insert is loaded. The cover then must be glued or otherwise secured to the shell to provide a closed container. The extra time required for the separate manufacturing and assembly operations results in added manufacturing costs for the package and ultimately for the product sold therein. The fact that the molded shells and covers must be shipped and stored in their molded form will also cause increased transportation and storage costs.

In a prior patent application, U.S. Ser. No. 25,012 filed Mar. 29, 1979 entitled "Carton with Adjustable Air Passages", assigned to the same assignee as the present invention, an improved package for controllably releasing active materials to the air is disclosed which has inner and outer slidable members constructed of a sheet material wherein the inner and outer members can be slidably moved between open and closed positions. The carton has a plurality of adjustable air passages and comprises: (a) a first tapered sleeve forming an outer carton unit, said first sleeve being closed at at least one end and having a plurality of spaced openings therein; and (b) a second tapered sleeve forming an inner carton unit, said second sleeve being nested within said first sleeve and being slidable between a first position and a second position, said second sleeve being closed at at least the end opposite said end closed in said first sleeve and having a plurality of spaced openings therein arranged complementarily to said spaced openings in said outer carton unit to align with the openings therein when said inner carton unit is in said first position, and to align with the spaces between said openings in said outer carton unit when said inner carton unit is in said second position.

When the openings are aligned, they permit air to circulate through the openings into the interior of the inner carton unit to permit the release or diffusion of material housed within the inner unit to the air. The tapered sleeves normally bind when moved relative to each other to preclude disassembly and when the openings are out of alignment, the diffuser is inoperative, as the openings in the inner unit are closed.

SUMMARY OF THE INVENTION

The present invention relates to an improved carton of the type having an inner and outer carton unit for use in dispensing an active material to the atmosphere.

The sides of the inner and outer unit do not taper but rather the closure seals on opposite ends of the inner carton unit extend beyond the side wall panels and are adapted to abut the top and bottom edges, respectively, of a slidable outer sleeve, approximately half the size of the inner unit, reciprocably mounted on the inner unit. The abutment of the inner and outer units precludes the units from becoming disassembled or separated.

The outer unit is imperforate, while the inner unit contains a plurality of openings on the lower half of two facing, major panels through which air can circulate about a cake of active material, such as air freshener material housed within the inner unit. In order to diffuse the active material to the atmosphere, it is only necessary to slide the inner unit relative to the outer carton unit or sleeve to expose the openings to the atmosphere. When not in use, the inner carton unit is slid relative to the outer sleeve to cover the openings.

BRIEF DESCRIPTION OF THE DRAWINGS

The invention will be better understood and its advantages will be more apparent from the following detailed description and claims, and from the accompanying drawings, wherein:

FIG. 1 is a plan view of a blank for forming the outer sleeve or unit of the carton of the present invention;

FIG. 2 is a plan view of a blank for forming the inner sleeve or unit of the carton of the present invention;

FIG. 3 is a perspective view of the outer sleeve of the carton folded from the blank of FIG. 1;

FIG. 4 is a perspective view of the inner sleeve of the carton folded from the blank of FIG. 2;

FIG. 5 is a perspective view of the assembled carton of the present invention with the openings in the inner sleeve closed to the atmosphere;

DETAILED DESCRIPTION OF THE PREFERRED EMBODIMENT

Figure 6:
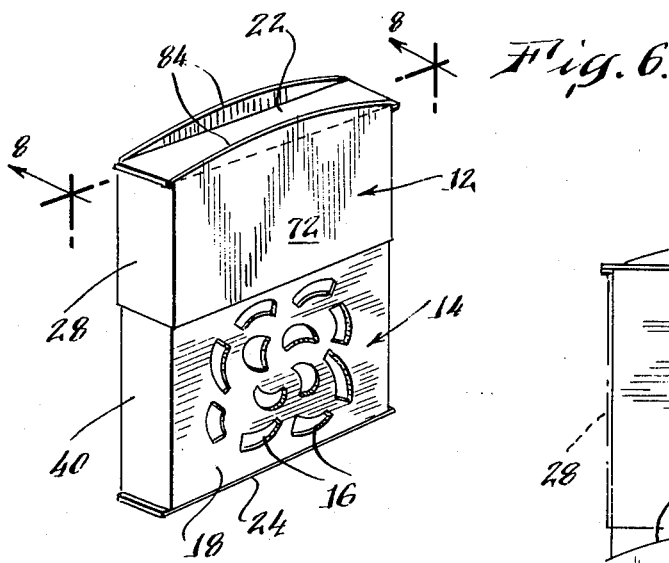
FIG. 6 is a view similar to FIG. 5 but with the outer sleeve moved relative to the inner sleeve to expose the openings in the inner sleeve.
Figure 7:
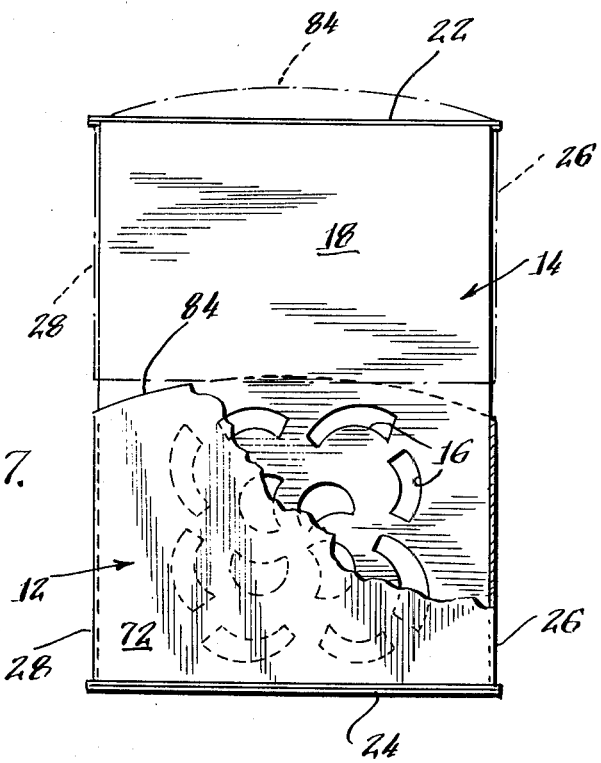
FIG. 7 is a front view in elevation of the carton of FIG. 5, partially broken away and in section.
Figure 8:
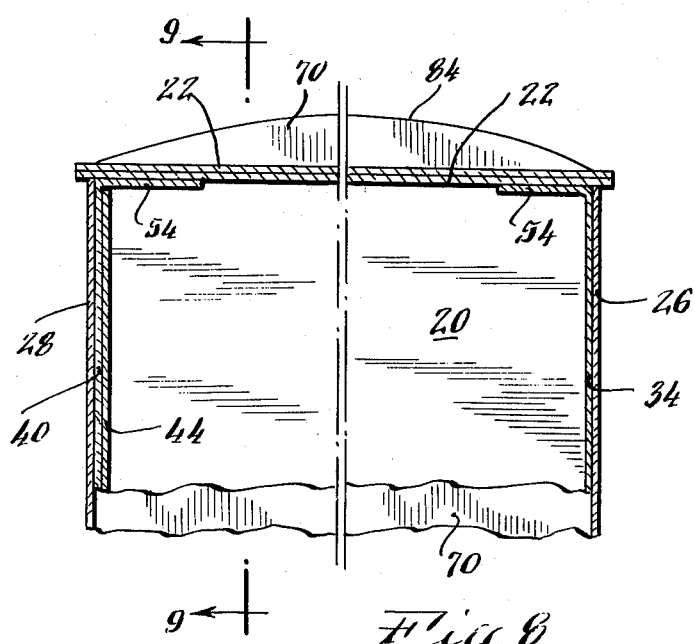
FIG. 8 is a cross-sectional view taken substantially along the plane indicated by line 8—8 of FIG. 6.
Figure 9:
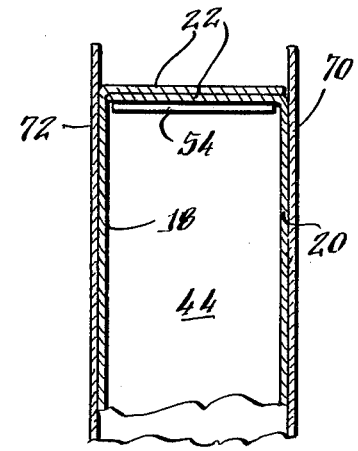
FIG. 9 is a cross-sectional view taken substantially along the plane indicated by line 9—9 of FIG. 8.

Referring now to the drawings in detail, wherein like numerals indicate like elements throughout the several views, the present invention provides a two component carton 10 consisting of an outer, imperforate sleeve 12 and a relatively slidable, inner carton unit 14 partially housed within the outer sleeve 12. Inner carton unit 14 has a plurality of openings 16 on facing major panels 18 and 20 through which air can circulate and contact a cake C of an active material, such as an insecticide or a room air freshener, and diffuse the material to the air when the inner carton unit 14 has one or more openings 16 exposed to the atmosphere.

The inner carton unit 14 is sealed by a pair of overlapping flaps 22 and 24 at each longitudinal end to hold the cake C within the interior of inner unit 14. The top and bottom pairs of flaps 22, 24 extend and project slightly beyond the edges of the parallel, major panels 18 and 20 so as to lie in the path of movement of the upper and lower perimeter, respectively, of the outer, imperforate sleeve 12. Accordingly, when the inner unit 14 is slid relative to the outer sleeve 12, the units will be precluded from separation and disassembly.

As shown in FIG. 2, the inner carton unit 14 is formed from a blank generally designated by the numeral 50. Blank 50 includes the major rectangular panels 18 and 20 containing openings 16 connected by a central rectangular panel 34. Panel 34 is connected by a fold line 36 to the left edge of panel 18, while it is connected by a fold line 38 to the right edge of rectangular panel 20.

Similarly, a rectangular panel 40 is connected by a fold line 42 to the right hand edge of panel 18, while a rectangular panel 44 is connected by a fold line 46 to the left hand edge of rectangular panel 20. The upper and lower sealing flaps 22 and 24, respectively, are foldably connected by hinge lines 48 and 52, respectively, to the upper and lower edges of major rectangular panels 18 and 20. Minor rectangular flaps 54 and 56 are connected by hinge lines 58 and 60, respectively, to the upper and lower edges of rectangular side panels 24 and 40, respectively.

The blank 50 is folded into a generally rectangular parallelepiped configuration as indicated in FIG. 4. The major panels 18 and 20 are folded about hinge lines 36 and 38, respectively, so that they face each other in parallel relationship. Panels 44 and 40 are then folded 90 ninety degrees about their respective hinge lines 46 and 42, overlapped and adhesively connected to lie parallel to and opposite side panel 34. The cake C can then be inserted within the enclosure thus formed between openings 16 and the ends of the enclosure sealed by folding flaps 22, 24, 54, and 56 about their respective fold lines, ninety degrees, and overlapping panels 22 and 24 on minor side flaps 54 and 56, respectively. The overlapping pairs of flaps 22 as well as 24 are adhesively sealed to each other.

The outer imperforate sleeve 12 is also formed from a unitary, planar, paperboard blank 100, illustrated in FIG. 1.

Blank 100 includes a pair of major, substantially rectangular panels 70 and 72 joined by a rectangular side wall panel 28. The panel 28 is connected to one edge of the panel 70 by a hinge line 74 while it is connected to an edge of panel 72 by a hinge line 76. Side wall panel 26 is connected to the opposite edge of the panel 70 by a hinge line 78. A third side wall panel 80 is connected to the opposite edge of the major rectangular panel 72 by a hinge line 82. The top edge of each panel 70, 72 is arcuate.

As indicated in FIG. 3, sleeve 12 is formed by wrapping blank 100 about panels 18, 20, 40 and 34 of inner unit 14 by folding panels 70 and 72 ninety degrees about hinge lines 74 and 76, respectively, so that they are spaced from each other in parallel relationship. The side panels 26 and 80 are then folded ninety degrees about hinge lines 78 and 80, respectively, so as to lie parallel to side panel 28, while side panel 26 is overlapped with panel 80 and adhesively connected thereto.

As shown in FIGS. 5 and 6, panels 70 and 72 of outer sleeve 12 are approximately half the length of panels 18 and 20 of inner unit 14. The openings 16 are formed in the lower half of panels 18 and 20. Panels 22 and 24 on the inner unit 14 are slightly larger in width than the major rectangular panels 18 and 20. Accordingly, when imperforate outer sleeve 12 is moved relative to inner unit 14, the lateral edges of panels 22 and 24 will abut the upper and lower edges of side panels 26 and 28 of outer sleeve 12 to retain the assembly of the outer and inner sleeves 12 and 14 as the sleeves are moved relative to each other to selectively expose (FIG. 6) or close (FIG. 5) the openings 16 to the atmosphere. When exposed (FIG. 6), the air freshener cake C can be diffused through openings 16.

What is claimed as new is:

1. A carton for dispensing an active material to the atmosphere comprising:

a first, imperforate sleeve having a pair of opposed major panels connected by a pair of opposed side wall panels forming an outer carton unit, said first sleeve being open at opposite longitudinal ends, and a second sleeve forming an inner carton unit having a pair of opposed major panels parallel to the major panels of said first sleeve and connected by a pair of opposed side wall panels, said opposed major panels including a plurality of openings and approximately half of the opposed major panels thereof, said second sleeve being generally of the same cross-sectional shape as said first imperforate sleeve and being received within said first sleeve and slidable therein between a first position defined by abutment of said first sleeve with a projecting sealed closure on one longitudinal end of said second sleeve whereby said openings in said second sleeve are exposed and a second position defined by abutment of said first sleeve with a projecting sealed closure on an opposite end of said second sleeve whereby said openings on said second sleeve are covered.

2. The carton of claim 1 wherein each of the sealed closures on the opposite ends of said second sleeve contains a panel projecting outwardly beyond the side edges of said major panels of said second sleeve to form stops in the path of movement of said first sleeve to preclude disassembly of said first and second sleeves.

3. The carton of claim 2 wherein said first sleeve opposed major panels are approximately one-half the length of the major panels of said second sleeve.

* * * * *